US00PP10864P

United States Patent [19]

Cosner et al.

[11] Patent Number: Plant 10,864

[45] Date of Patent: Apr. 20, 1999

[54] LOTUS VINE PLANT NAMED 'AMAZON SUNSET'

[76] Inventors: Harlan B. Cosner; Sue L. Cosner, both of P.O. Box 173, Broadbent, Oreg. 97414

[21] Appl. No.: 08/938,580

[22] Filed: Sep. 26, 1997

[51] Int. Cl.[6] ..... A01H 5/00

[52] U.S. Cl. ..... Plt./226

[58] Field of Search ..... Plt./54.1, 226

*Primary Examiner*—Howard J. Locker

*Assistant Examiner*—Kent L. Bell

[57] ABSTRACT

A new and distinct cultivar of Lotus Vine plant named 'Amazon Sunset', characterized by its soft orange flowers; numerous flowers per plant; long flowering period; freely branching, dense plant habit; and spreading, pendulous and trailing habit.

1 Drawing Sheet

The present invention relates to a new and distinct cultivar of Lotus Vine plant, botanically known as *Lotus berthelotii*x *Lotus maculata*, and hereinafter referred to as 'Amazon Sunset'.

The new cultivar is a product of a planned breeding program conducted by the inventors in Coquille, Oreg. The objective of the breeding program is to create new Lotus Vine cultivars having unique flower colors and long flowering period.

The new cultivar originated from a cross made by the inventors in May, 1994, of the red-flowered *Lotus berthelotii* cultivar 'Red Flash' (not patented) as the male, or pollen, parent with an unnamed proprietary *Lotus maculata* seedling selection with yellow flowers as the female, or seed, parent.

The cultivar Amazon Sunset was discovered and selected by the inventors as a flowering plant within the progeny of the stated cross in a controlled environment in Coquille, Oreg. The selection of this plant was based on its unique flower colors and long flowering period.

Asexual reproduction of the new cultivar by terminal cuttings taken in a controlled environment in Coquille, Oreg., has shown that the unique features of this new Lotus Vine are stable and reproduced true to type in successive generations.

COMPARISON

Comparing the instant plant to the plant in the co-pending U.S. Plant Patent application Ser. No. 08/938,579, the instant plant is distinct as follows:

a) from a distance of a few feet, the instant plant's flowers have a distinguishable red/yellow bi-color appearance while the co-pending plant's flowers take on an apricot color;

b) the instant plant produces more flowers over a longer flowering time.

VERNALIZING

Typical requirements are at least 30 days with night temperatures below 40° F. and above 32° F.

The following traits have been repeatedly observed and are determined to be the unique characteristics of 'Amazon Sunset'. These characteristics in combination distinguish the new Lotus Vine as a new and distinct cultivar:

1. Soft orange flowers.
2. Numerous flowers per plant.
3. Long flowering period.

4. Freely branching, dense plant habit.
5. Spreading, pendulous and trailing habit.

The new Lotus Vine has not been observed under all possible environmental conditions. The phenotype may vary significantly with variations in environment such as temperature, light and fertility level, without, however, any variance in genotype.

BRIEF DESCRIPTION OF THE PHOTOGRAPHS

The accompanying colored photographs illustrate the overall appearance and flower color of the new Lotus Vine, showing the colors as true as it is reasonably possible to obtain in colored reproductions of this type.

The photograph at the top of the sheet comprises a side perspective view of typical plants of the new Lotus Vine in a hanging basket container.

The photograph at the bottom of the sheet comprises a side perspective view of typical leaves and flowers of the new Lotus Vine. Flower and foliage colors in the photographs may appear different from the actual colors due to light reflectance.

DETAILED BOTANICAL DESCRIPTION

The following observations, measurements, values, and comparisons describe plants grown in Coquille, Oreg., grown under double layer of polyethylene with day temperatures ranging from 23 to 30° C. and night temperatures ranging from 10 to 18° C., and light levels ranging from 3,000 to 5,000 footcandles.

In the following description, color references are made to The Royal Horticultural Society Colour Chart except where general terms of ordinary dictionary significance are used.

Botanical classification: *Lotus berthelotii*x*Lotus maculata* cultivar 'Amazon Sunset'.

Parentage:

*Male or pollen parent.*—*Lotus berthelotii* cultivar Red Flash, not patented.

*Female or seed parent.*—Unnamed yellow flowered *Lotus maculata* proprietary seedling selection.

Propagation:

*Type cutting.*—Terminal cuttings.

*Time to initiate roots.*—32 to 35 days at a temperature of 21° C.

*Time to develop roots.*—About 70 days at a temperature of 21° C.

*Rooting habit.*—Fine, fibrous, and well-branched.

Plant description:

*Form.*—Spreading, pendulous and trailing shrub. Plants grown in hanging baskets typically measure about 70 cm wide×70 cm long.

*Growth habit.*—Moderately vigorous. Dense and bushy growth.

*Branching habit.*—Freely branching with lateral branches forming at every node.

*Lateral branches.*—Diameter: About 2.5 mm. Internode length: About 2.25 cm. Texture: Very fine silvery pubescence. Color (with pubescence): 138A/138B with reddish overtones.

*Foliage description.*—Alternate half-whorls, about 7 per node. Leaflet length: About 1.5 cm. Leaflet width: About 1 mm. Shape: Needle-like with acute apex, sessile with entire margin. Texture: Very fine silvery pubescence. Color (with pubescence): Young leaflets, upper surface: 191A. Young leaflets, lower surface: 191A. Mature leaflets, upper surface: 191A. Mature leaflets, lower surface: 191A.

Flower description:

*Flower type and habit.*—Flowers arranged in axillary umbels with usually three flowers per umbel. Flowers papilionaceous and symmetrical with two upper petals fused, two lateral petals and a lower petal. Freely and continuously flowering. Flowers numerous and self- cleaning.

*Flowering season.*—Spring and again in fall.

*Flower length.*—About 2.75 cm.

*Flower width.*—About 6 mm.

*Flower depth (height).*—About 2 cm.

*Flower buds.*—Length: About 1 cm. Diameter: About 2 mm. Shape: Elongated. Color: Whitish green.

*Petals.*—Quantity: Five, upper two petals fused, two lateral petals and one lower petal. Apices acuminate, margins entire. Texture: Waxy, smooth. Color, outer surfaces: Upper fused petals: 35A/35B at base, towards apex, 46A with 59A at apex. Lateral petals: 33A at base, 17A at center, 46A at apex. Lower petals: Edges, 17A, center, 187A. Color, inner surfaces: Upper fused petal close to 180A at apex, 179C at base. Lateral petals have markings close to 179C and 163C at base; 17B and 179A in middle section, generally in alternating stripes; and 179A at apex. Lower curved petal is close to 150B at base, changing to 172B; center stripe close to 183B; markings of 173A and close to 167A appear in center portion of outer edges.

*Sepals.*—Quantity: Usually five, fused at base into a star-shaped calyx. Texture: Very fine pubescence. Color: 146C.

*Peduncles/pedicels.*—Peduncles are about 1 cm long and 2 mm in diameter; pedicels are about 8 mm long and 1 mm in diameter; a cluster of 4 to 7 leaves are at the apex of each peduncle where pedicels attach; pedicels attach to base of calyx; peduncle color is 146B; pedicel color is 146C.

*Reproductive organs.*—Stamens: Quantity: Usually ten. Anther shape: Oblong. Anther size: About 1 mm. Anther color: Yellow. Amount of pollen: Abundant. Pollen color: Very light yellow. Pistils: Quantity: One. Pistil length: About 4 cm. Stigma color: Greenish yellow. Style color: Green at base, white towards apex.

Disease resistance: Under commercial conditions, neither resistance or susceptibility to pathogens have been tested. No problems related to pathogens have been noticed.

It is claimed:

1. A new and distinct Lotus Vine plant named 'Amazon Sunset', as illustrated and described.

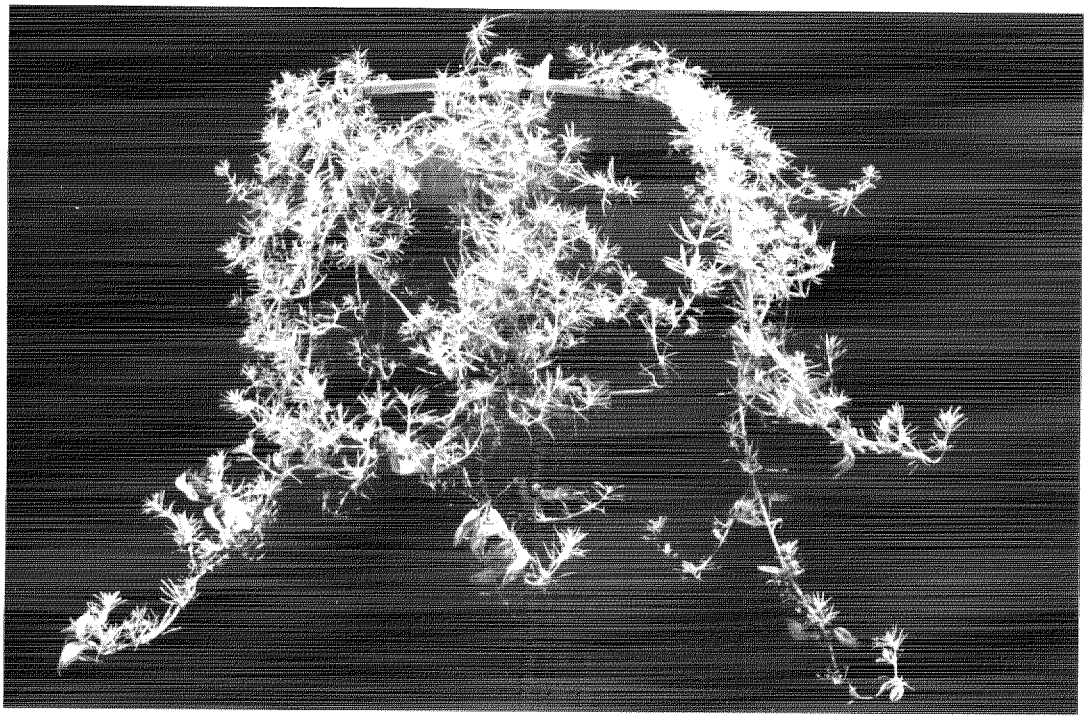
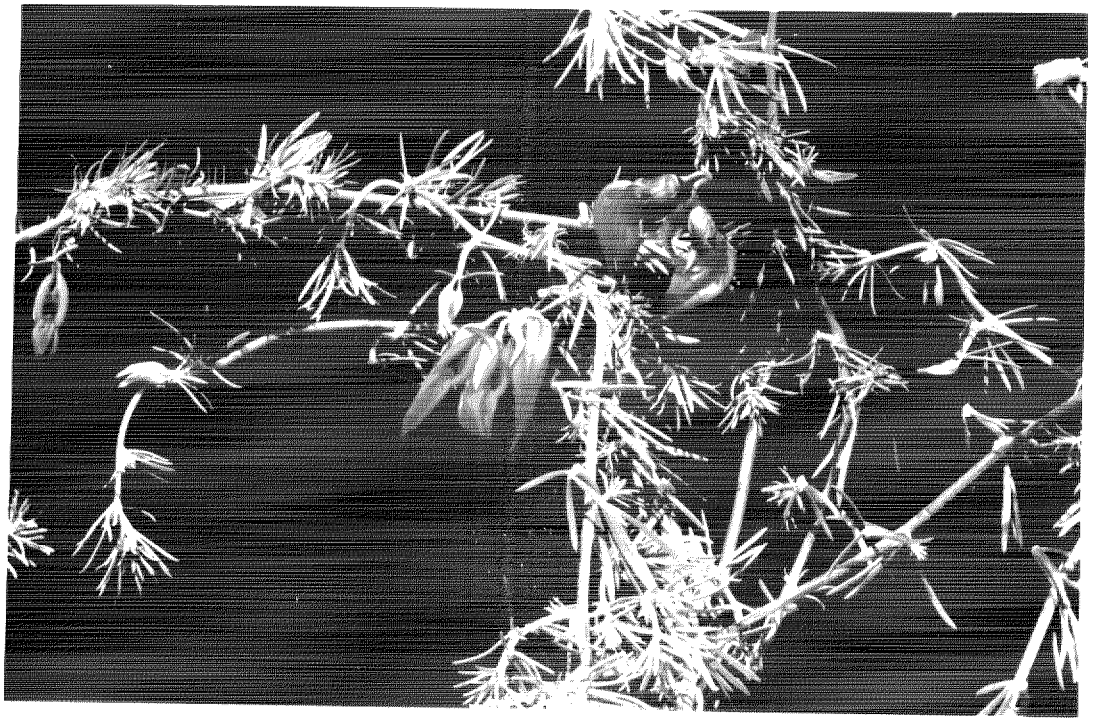

* * * * *